United States Patent [19]

Ryan et al.

[11] 4,055,183
[45] Oct. 25, 1977

[54] DISPOSABLE DIAPER WITH CUTOUT PAD AT TAPE ATTACHMENT AREA

[75] Inventors: Arthur Sensor Ryan, Longview; Raymond August Van Vliet, Castle Rock, both of Wash.

[73] Assignee: Weyerhaeuser Company, Tacoma, Wash.

[21] Appl. No.: 729,230

[22] Filed: Oct. 4, 1976

[51] Int. Cl.² .................... A41B 13/02; A61F 13/16
[52] U.S. Cl. .................................... 128/287; 128/284
[58] Field of Search ............... 128/287, 284, 290 R, 128/296, 290 P

[56] References Cited

U.S. PATENT DOCUMENTS

| | | | |
|---|---|---|---|
| 3,900,031 | 8/1975 | Endres | 128/287 |
| 3,971,380 | 7/1976 | Tritsch | 128/287 |
| 3,995,639 | 12/1976 | Cheslow | 128/287 |
| 3,999,547 | 12/1976 | Hernandez | 128/284 |
| 4,002,172 | 1/1977 | Feldman | 128/284 |

Primary Examiner—Aldrich F. Medbery

[57] ABSTRACT

An improved diaper fastener system has particular application to a conventional disposable diaper having a generally rectangular shaped absorbent pad or filler disposed between a fluid-permeable cover sheet and a thermoplastic film backing sheet. The fastener system is comprised of a pair of conventional pressure-sensitive fastening tapes but the fixed portions of the tapes are positioned to coincide with cutout regions within the filler material. The regions within the cover sheet and within the backing sheet that are coplaner with the cutout regions in the filler material are integrally joined together with either a heat sealed bond or by using an appropriate adhesive. The bonds between the backing sheet and the cover sheet in the regions where the tapes will be fixed to the diaper serve to better distribute forces exerted on the free ends of the tapes, particularly during the diapering process.

8 Claims, 5 Drawing Figures

DISPOSABLE DIAPER WITH CUTOUT PAD AT TAPE ATTACHMENT AREA

BACKGROUND OF THE INVENTION

This invention relates generally to disposable diapers and more particularly to an improved fastening system for such diapers.

Conventional disposable diapers, in one popular construction, are comprised of a generally rectangular absorbent pad or a filler disposed between a fluid-permeable, body-facing top sheet, and a fluid-impermeable plastic film backing sheet. The filler may be comprised of typical commercially available fluff pulp while the top sheet may be comprised of a typical commerically available non-woven material and the backing sheet can be comprised of a thin sheet of polyethylene. At the side edges of the diaper the backing sheet can be folded around the edge and sealed so that a narrow strip overlies the top sheet while at the ends the backing sheet can extend loosely past the top and bottom edges providing a foldable flap to tuck in against the backing sheet upon diapering the infant.

The tapes, in a typical construction, are adhered at one end to the backing sheet while the other end can extend outwardly from the side edge or it can be folded back and adhered to a release liner fixed to the opposite side. A major problem with tapes that are fixed solely to the plastic film backing sheet is that when a person applies tension to the tape, stresses are created within the plastic film and it is likely to rupture and tear making the diaper unusable. When all of the stress is applied to the thin film, especially when attempting to pull the diaper tight about the waist of the infant, it can easily tear.

This problem has been recognized and at least two solutions have been proposed. One solution may be seen by referring to U.S. Pat. No. 3,867,940 issued Feb. 25, 1975 to Mesek et al. wherein a reinforcing scrim having a higher modulus of elasticity than the thin film backing sheet is adhered to the thin film in a location at least in the vicinity of where the tape is adhered to the thin film. This construction allows some of the stress to be taken by the stronger reinforcing material. Another solution may be seen by referring to U.S. Pat. No. 3,900,031 issued Aug. 19, 1975 to Endres et al. in which the tape tabs are attached to the backing sheet in an area where the top sheet is adhered thereto along the entire top edge. In the Endres et al. construction the filler material terminates so that it does not extend all the way in the longitudinal direction to the sealed top end margin of the diaper. Each of these tape constructions operates to solve the problem for the particular diaper construction; however, the diaper construction of the present invention is different than both Mesek et al. and Endres et al. and consequently neither tape construction is suitable to adequately reduce or prevent the tearing of the backing sheet.

Accordingly, from the foregoing an object of the present invention is to provide an improved diaper fastening system that reduces tearing of the plastic film backing sheet.

Another object of this invention is to provide a reinforced structure at the fixed end of each tape while leaving the end edge of the backing sheet free to be folded.

These and other objects of the invention will become more apparent upon reading the description to follow while referring to the drawings.

SUMMARY OF THE INVENTION

Briefly stated, this invention is comprised in one form of a disposable diaper of the type having a generally rectangular absorbent pad or filler disposed between a fluid-permeable body-contacting top sheet and a fluid-impermeable plastic film backing sheet together with a pair of pressure-sensitive fastening tapes with one end of each tape fixed to the backing sheet in a region where the filler material has been cut out and where the backing sheet and top sheet are bonded together into an integral two-layer structure. The top edge of the filler material is at a longitudinal location above the tape ends fixed to the backing sheet.

DESCRIPTION OF THE PREFERRED EMBODIMENTS

Figure 1:
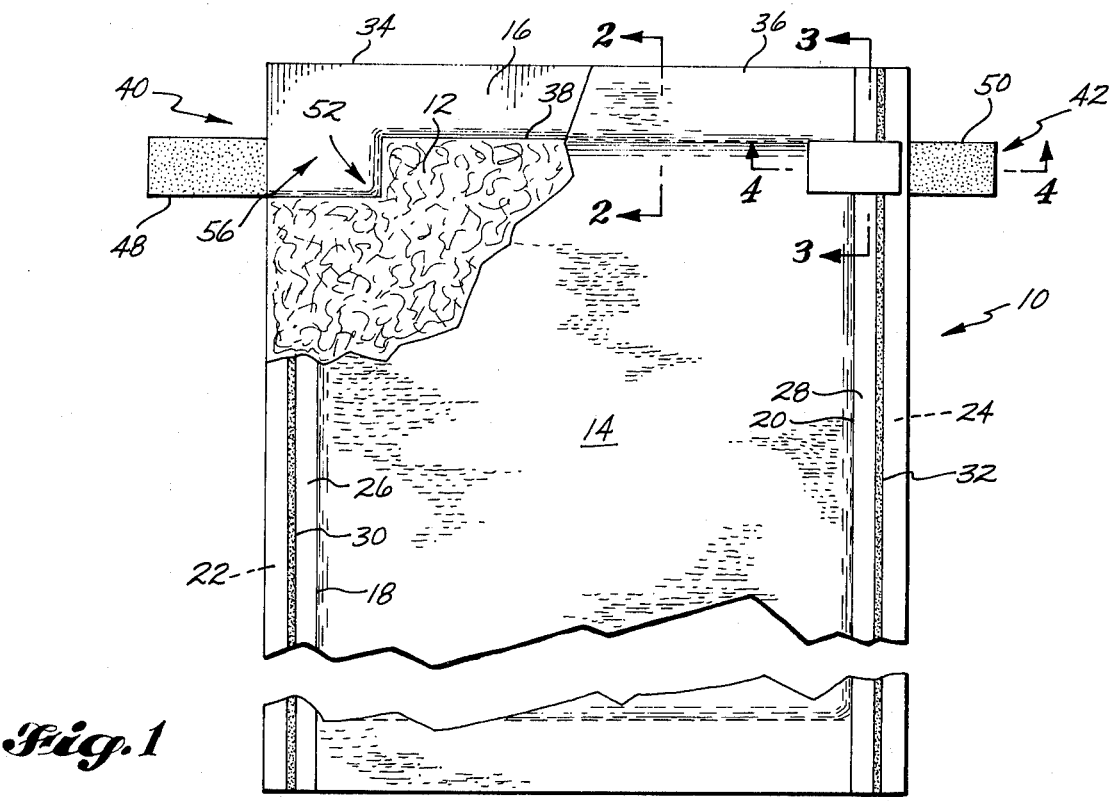
FIG. 1 is a partially cutaway plan view looking at the body-contacting side of the disposable diaper.

Referring first to FIG. 1, a general description will be given of the disposable diaper comprising a part of the present invention. As earlier mentioned, the basic rectangular structure of the diaper, which is generally indicated at 10, is conventional in nature and can be comprised of a rectangular absorbent pad or filler 12 disposed between a fluid-permeable body-contacting top or cover sheet 14 and a fluid-impermeable plastic film backing sheet 16. The top sheet 14 is substantially the same length as the backing sheet 16 while it is substantially the same width as the absorbent pad 12. The backing sheet 16 is greater in width than pad 12 and top sheet 14 and each long edge 18, 20 of backing sheet 16 is folded to overlie narrow marginal portions 22, 24 of top sheet 14. The flaps 26, 28 formed from backing sheet 16 are bonded to top sheet 14 along longitudinal bonding lines 30, 32 by any suitable adhesive such as a hot melt.

Figure 2:
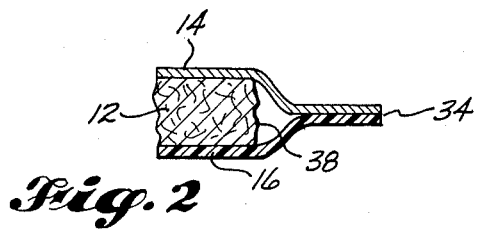
FIG. 2 is a sectional view taken along line 2—2 of FIG. 1 and shows the top transverse edge details.
Figure 3:
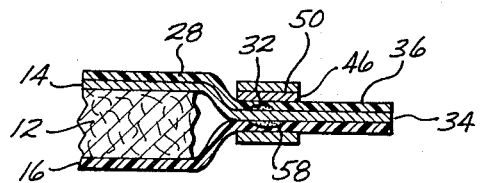
FIG. 3 is also a sectional view taken along line 3—3 of FIG. 1 and shows the details through the fastening area.

The absorbent pad 12 is shorter at both ends of diaper 10 than the coterminal transverse edges of top sheet 14 and backing sheet 16. As may be seen by referring to FIG. 2, the top edge 34 of diaper 10 is essentially a foldable flap 36 comprised of the bonded together top sheet and backing sheet top marginal portions. The absorbent pad 12 terminates in the longitudinal direction substantially along a transverse edge 38. The transversely extending flap 36 is often used by a parent when diapering an infant as a flap to fold over and tuck between the infant's body and the top sheet after attachment about the infant. The flap 36 in the tucked position provides a sealing function about the transverse ends of diaper 10 when in use.

Figure 4:
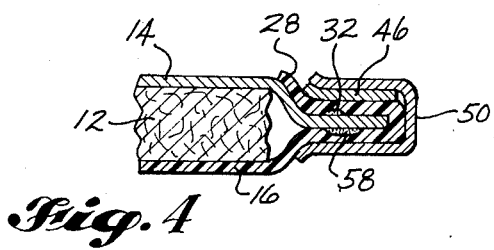
FIG. 4 is another sectional view taken along line 4—4 of FIG. 1 and shows further details through the fastening area.

At transversely opposed locations toward the top edge 34 of diaper 10, but spaced a longitudinal distance therefrom, are a pair of pressure-sensitive fastening tapes 40, 42. Tapes 40, 42 are also of a conventional structure with one end permanently fixed by an adhesive to a small portion of the plastic film backing sheet 16 on the outer side thereof. In the embodiment depicted in the drawings, a pair of release liners 44, 46 (one of which is not shown) are fixed to the diaper 10 at a position on the body-contacting surface so as to overlie and be coplanar with the tab ends of each tape 40, 42 when tabs 48, 50 are in their folded closed positions (see FIG. 4).

At the tape attachment areas on diaper 10 the diaper structure is modified according to the present invention. Cutout regions 52, 54 within the absorbent pad 12 are positioned at opposite transverse corners and are sized so as to be slightly larger than the planar size of the fixed portion of each tape 40, 42. The cutout regions 52, 54 are positioned longitudinally below the edge 38 and provide areas closer to the transverse center line of diaper 10 where the tapes 40, 42 will be attached. The top sheet 14 extends over the cutout regions 52, 54 and to its conventional boundaries along the longitudinal sides of absorbent pad 12 and to the ends of backing sheet 16. Within the cutout regions 52, 54 the areas of the top sheet overlaying the areas of the backing sheet are bonded together into integral reinforced tape attaching bases 56, 58. A spot of hot melt adhesive 60 at each area can be applied so as to bond the top sheet and backing sheet together. Any other suitable bonding means may be employed such as heat sealing. The primary purpose is to provide the integral structure so that when outward tension is exerted on the free end of a tape at least the major stress is transferred through the joint to the top sheet. The top sheet material has a higher transverse strength in tension than the plastic backing sheet and therefore can withstand greater stresses.

With the tapes 40, 42 attached within cutout regions 52, 54 at positions below the edge 38 of absorbent pad 12 longitudinal tearing of the plastic backing sheet is minimized for the normal application forces. This feature together with the stress transferring function provided by the attaching bases 56, 58 offers a disposable diaper with pressure-sensitive tapes that minimize tearing of the thin plastic backing sheet.

Figure 5:
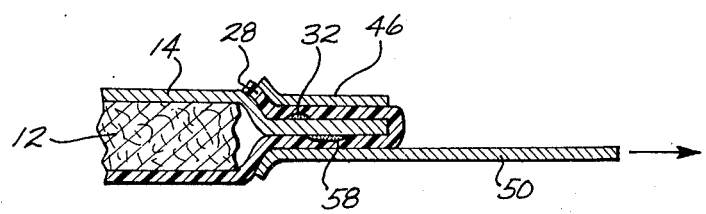
FIG. 5 is yet another sectional view taken through a plane similar to that of FIG. 4 but showing a tape tab transversely extended and with a force applied.

When a parent is ready to use diaper 10, the free end of a tape is peeled back from its respective release liner 44, 46 (see FIGS. 4 and 5) in typical fashion. The free end is then placed under tension as shown by the force vector arrow in FIG. 5 while it is being positioned over the other end of a diaper corner.

The cutout regions 52, 54 within the absorbent pad can take other planar shapes than shown in FIG. 1. For example a triangular cutout may be employed as may curvilinear cutouts. The primary requirement is that each cutout provide a sufficient area for bonding the top sheet to the backing sheet and that it be positioned below the uppermost point along pad edge 38.

While a preferred embodiment of the present invention has been described together with some alternative structures, it is to be understood that many changes and modifications may be made without departing from the scope of the invention. All such modifications are intended to be included within the scope of the appended claims.

What is claimed is:

1. A disposable diaper of the type having a generally rectangular shaped absorbent pad disposed between a fluid-permeable cover sheet and a thin plastic backing sheet together with a pair of pressure-sensitive fastening tapes for securing the diaper about a person has the improvement comprising:
    a pair of cutout regions within the absorbent pad positioned at the corners thereof where said tapes are fixedly secured to said backing sheet; and
    means to bond together the regions of the cover sheet overlaying the backing sheet within the cutout regions into integral tape attaching bases to which a portion of said fastening tapes are attached, whereby tension exerted on the free end of a tape will be transferred, at least in part, to the cover sheet.

2. A disposable diaper as in claim 1 wherein the top edge of said absorbent pad is longitudinally spaced from the top edge of said backing sheet.

3. A disposable diaper as in claim 1 in which said cutout regions are sized so as to be slightly larger than the planar size of the fixedly secured ends of said tapes.

4. A disposable diaper as in claim 1 wherein said cutout regions are positioned longitudinally below the top edge of said absorbent pad.

5. A disposable diaper as in claim 1 wherein the bonding means is a spot of hot melt adhesive positioned so as to join the backing sheet to the cover sheet.

6. A disposable diaper as in claim 1 wherein said cutout regions have a rectangular planar outline.

7. A disposable diaper as in claim 1 wherein said cutout regions have a triangular planar outline.

8. A disposable diaper as in claim 1 wherein said cutout regions have a curvilinear planar outline.

* * * * *